United States Patent [19]

Gandi et al.

[11] 4,300,550

[45] Nov. 17, 1981

[54] SUCTION AND OXYGENATION CATHETER

[75] Inventors: Robert A. Gandi, New York, N.Y.; Anthony P. Martino, Wayne, N.J.

[73] Assignee: Becton, Dickinson and Company, Paramus, N.J.

[21] Appl. No.: 128,143

[22] Filed: Mar. 7, 1980

Related U.S. Application Data

[63] Continuation of Ser. No. 900,144, Apr. 26, 1978, abandoned.

[51] Int. Cl.³ ............................................. A61M 16/00
[52] U.S. Cl. ................................ 128/207.18; 128/276
[58] Field of Search ................... 128/140 N, 184, 198, 128/206, 240, 276, 348, 349 R, 350 R, 202.28, 207.14–207.18

[56] References Cited

U.S. PATENT DOCUMENTS

| | | | |
|---|---|---|---|
| 2,175,726 | 10/1939 | Gebauer | 128/349 B |
| 2,614,563 | 10/1952 | Devine, Jr. | 128/276 |
| 3,297,027 | 1/1967 | Rüsch | 128/202.28 |
| 3,319,628 | 5/1967 | Halligan | 128/350 R |
| 3,626,928 | 12/1971 | Barringer | 128/276 |
| 4,022,219 | 5/1977 | Basta | 128/207.14 |
| 4,036,210 | 7/1977 | Campbell et al. | 128/207.16 |
| 4,037,599 | 7/1977 | Raulerson | 128/240 |
| 4,072,146 | 2/1978 | Howes . | |
| 4,139,012 | 2/1979 | Zahorsky | 128/350 R |

*Primary Examiner*—C. Fred Rosenbaum

[57] ABSTRACT

A catheter for use in simultaneous tracheal oxygenating and aspirating a patient. The catheter includes an elongated flexible tube arrangement adapted to have at least one end portion extended into the tracheal passage of a patient. The tube arrangement has two separate lumens therethrough. One lumen has at least one opening in the one end portion and is adapted to be connected at the other end of the tube arrangement to a source of suction to permit aspiration of material from the patient through the one lumen. The other lumen has at least one opening at the other end and is adapted to be connected at the other end to a source of oxygen to permit simultaneous oxygenating of the patient through the other lumen while the patient is aspirated through the one lumen.

6 Claims, 7 Drawing Figures

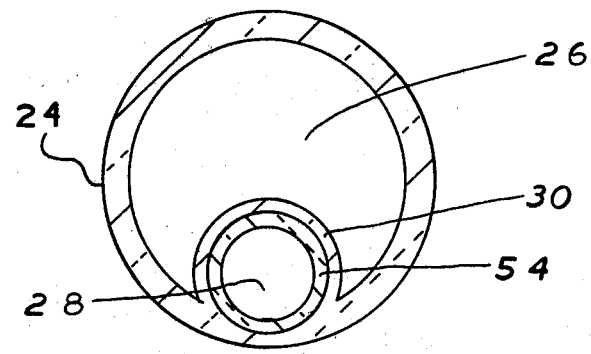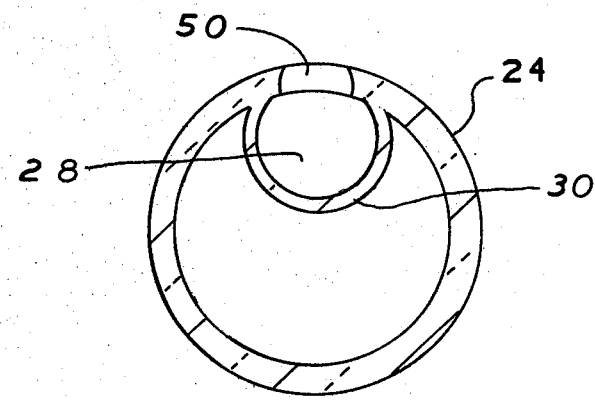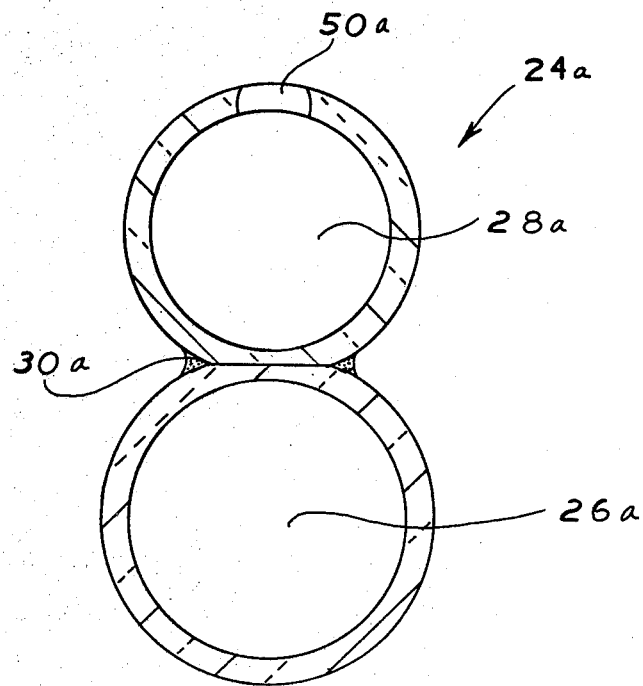

SUCTION AND OXYGENATION CATHETER

This is a continuation of application Ser. No. 900,144, filed Apr. 26, 1978, and now abandoned.

BACKGROUND OF THE INVENTION

There are many known devices and techniques presently employed for the purpose of catheterization or intubation of a patient to reach the tracheal passageway for a number of purposes. Conventionally it is often desirable to apply a suction and aspirate fluids including mucous and secretions from the bronchial/tracheal area. Also, it is often desirable to use a catheter introduced into the tracheal area for purposes of supplying the patient with oxygen to improve difficult breathing conditions.

The most widely used current technique is to preoxygenate for 1 to 5 minutes with a mask, a mouthpiece, and a conventional oxygen catheter arrangement. After this procedure is completed, the oxygen delivery device is removed and a tracheal suction catheter is introduced which in turn not only removes the mucous and secretions but also often robs the patient of much needed oxygen. This naturally can cause problems for the patient. Accordingly, it is desirable to have the patient supplied with the necessary oxygen for ease of breathing and also provide for removal of mucous and secretions and other matter clogging the breathing passageways.

Thus, it would be extremely advantageous to provide a catheterization system which permits a patient to be oxygenated simultaneously with an aspiration procedure thus supplying the patient with much needed oxygen at a critical time. A combination device of this type which is of simple and low cost construction lending itself to disposability and ease of use would be extremely advantageous and desirable in the medical instrument field.

SUMMARY OF THE INVENTION

With the above background in mind, it is among the primary objectives of the present invention to provide a combination oxygenating and aspirating catheter which allows a patient to be oxygenated simultaneously with an aspiration procedure thus supplying the patient with the needed oxygen at a significant point of time. The device allows for a constant or intermittent delivery of oxygen or air while the suctioning procedure is being performed. By adjusting to proper relative flow rates and negative pressure settings on the support equipment it is possible to maintain the patient's $PO_2$ in the blood at equilibrium or even increase it depending on the patient's condition.

It is an objective to provide a combination catheter of the above type which is of simple construction and which can be easily and efficiently utilized with conventional equipment. It is designed to combine two procedures into one time saving procedure, namely, oxygenation of a patient and tracheal/bronchial suctioning. The catheter is designed for use with existing support equipment or devices, such as pumps, regulators, humidifiers, endotracheal and tracheal tubes. Furthermore, the device can be used as a standard aspirating catheter if air or oxygen delivery is not required, for example in emergency use. The device is formed of low cost material, has a minimum construction cost and is formed to a standard size.

In short, a double lumen tube arrangement is provided with each lumen being independent of the other, that is not interconnected. One lumen is designed to provide a means of aspirating gases, liquids, and other materials from a patient, while the other lumen is designed to carry oxygen or air to a patient simultaneously with the suctioning procedure.

More specifically, a catheter is provided for use in oxygenating and aspirating a patient. The catheter includes an elongated flexible tube arrangement adapted to have at least one end portion extended into the tracheal/bronchial passage of a patient. The tube arrangement has two separate lumens therethrough. One lumen has at least one opening in the one end portion and is adapted to be connected at the other end of the tube arrangement to a source of suction to permit aspiration of material from the patient through the one lumen. The other lumen has at least one opening at the other end and is adapted to be connected at the other end to a source of oxygen to permit oxygenating of the patient through the other lumen while the patient is aspirated through the one lumen.

With the above objectives among others in mind, reference is made to the attached drawings.

BRIEF DESCRIPTION OF THE DRAWINGS

In The Drawings:

FIG. 3 is a sectional end view thereof taken along the plane of line 3—3 of FIG. 2;

FIG. 4 is a sectional end view thereof taken along the plane of line 4—4 of FIG. 2;

FIG. 6 is a sectional end view of the embodiment of FIG. 5 taken along the plane of line 6—6 of FIG. 5; and FIG. 7 is a fragmentary partially sectional plan view of a second alternative embodiment of the catheter of the invention.

DESCRIPTION OF THE PREFERRED EMBODIMENTS

Figure 1:
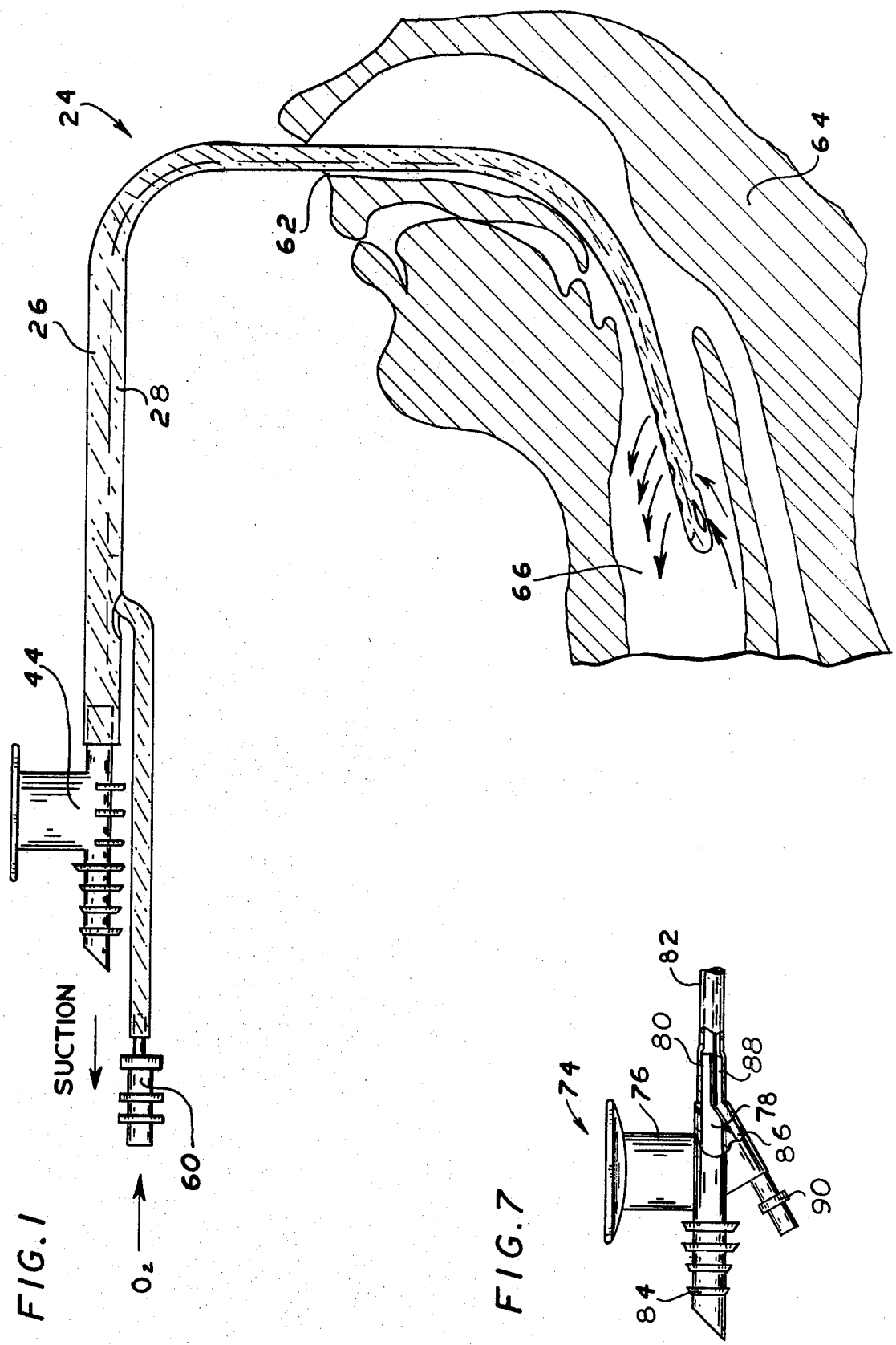
FIG. 1 is a perspective view of the catheter of the invention in position in the patient with arrows showing the direction of oxygen flow and flow due to suction.
Figure 2:
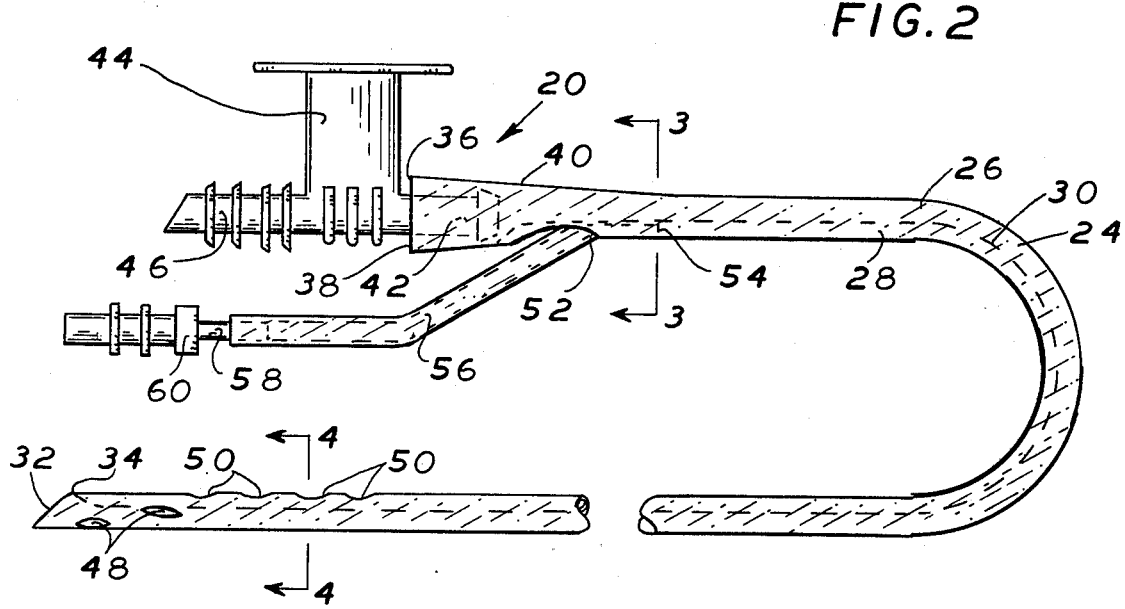
FIG. 2 is a plan view of one embodiment of the catheter of the invention.

Catheter 20 as depicted in FIGS. 1–4 includes a tube arrangement in the form of a plastic tube 24 having two separate lumens therethrough. The larger lumen 26 is spaced from the smaller lumen 28 by means of an interior wall 30. Lumen 26 terminates in an opening 32 in the beveled tip 34 or, if desired in a straight tip. There is an opening 36 at the terminal edge 38 of the other end of the lumen 26. The portion adjacent to edge 38 extends outwardly toward the edge to form portion 40 which is adapted to receive one end 42 of a conventional connector 44 therein in frictional engagement therewith. The other end portion 46 of connector 44 is adapted for connection to a source of suction. Thus, a through passageway is formed through tube 24 from end to end to form lumen 26.

Two openings 48 are positioned adjacent to beveled edge 32 and in the side walls of tube 24 to provide additional openings to lumen 26 to enhance the suctioning action through the lumen as the catheter is utilized. The number of openings 48 is a matter of choice.

The other, smaller lumen 28 terminates at a closed end adjacent to beveled edge 42 but has four adjacent openings 50 in the side wall of tube 24 spaced from openings 48 so as to avoid interference with the suctioning action through openings 48. Once again the number of openings 50 is a matter of choice.

Similarly, the other end of lumen 28 terminates short of edge 38 at the other end of tube 24 and ends at a larger side opening 52 to provide communication with lumen 28. One end 54 of a connector tube 56 having a passageway therethrough is extended through opening 52. The other end of connector tube 56 is adapted to receive one end portion 58 of a conventional connector 60 for a conventional source of oxygen. Thus, oxygen can be introduced through the passageway in connector 60, through connector or tube 56 and through lumen 28 to exit through openings 50. By providing side opening 52 spaced from the opening 36 and the end of tube 24, there is no interference between the suctioning action and the supply of air or oxygen.

In use as depicted in FIG. 1, tube 24 is inserted into the nasal passage 62 of a patient 64 and the tube 24 is formed of a flexible material so that it can be easily extended into the throat of the patient until it reaches the tracheal passageway 66. Connector 44 is attached in a conventional manner to a source of suction and connector 60 is similarly connected in a conventional fashion to a source of air or oxygen. Thereafter, simultaneously or intermittently, as desired, suction force is applied through lumen 26 and oxygen supplied through lumen 28 so that flow paths are derived as shown by the arrows in FIG. 1. The suctioning force and oxygen supply force are regulated in a conventional manner so that they can be applied simultaneously, continuously or intermittently. With both of the forces applied as shown in FIG. 1, materials are aspirated through openings 32 and 48, through lumen 26 and through connector 44 to remove mucous, secretions and other materials from the patient. Simultaneously, oxygen or air is supplied through connector 60, through connector tube 56 and through lumen 28 until it exits through openings 50 directly into the tracheal passageway to improve breathing conditions for the patient.

With the lumens both included as one unitary tube 24 ease of introduction of the tube arrangement to the patient is facilitated. Additionally, the flexible tube 24 can be formed of a conventional flexible catheter material such as polyethylene, polyvinyl chloride or rubber and accordingly is disposable in nature being of inexpensive material, inexpensively manufactured and efficient and inexpensive to utilize.

Figure 5:
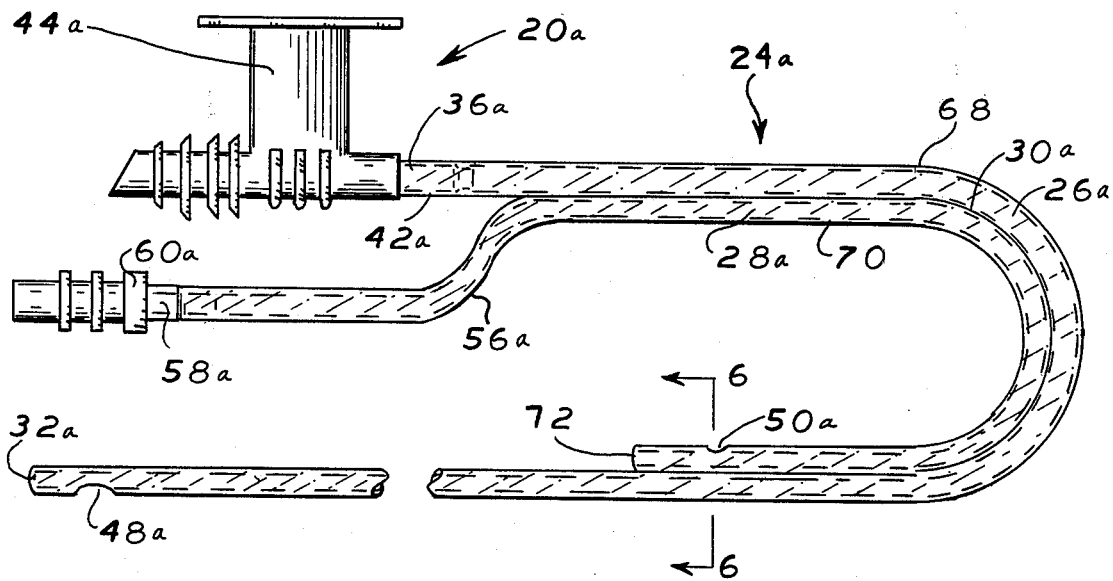
FIG. 5 is a plan view of an alternative form of the catheter of the invention.

An alternative catheter 20a is depicted in FIGS. 5 and 6 and operates in a similar fashion as the embodiment of FIGS. 1-4. Differences reside in the construction of the tube arrangement. Like parts to the embodiment of FIGS. 1-3 bear the same numerals with the addition of the subscript "a". Tube 24a can be formed of the same material as tube 24 and accordingly has the same advantages thereof, is also inexpensive in manufacture, efficient to use and is inexpensive in ultimate operation thus lending itself to disposability. The tube 24a is formed of two separate tube elements 68 and 70. These tubes are interconnected to one another in a conventional fashion such as by an epoxy or adhesive to form a wall 30a therebetween. Alternatively the tube elements 68, 70 may be co-extruded. Tube 68 has a lumen 26a therethrough and tube 70 has a lumen 28a therethrough. Tube 68 has an opening 32a at one end and a side opening 48a adjacent thereto for communication with lumen 26a. The other end of tube 68 has an opening 36a therein for receipt of one end portion 42a of a conventional connector 44a for a source of suction. The connector 44a has a passageway therethrough thus providing a through passageway from end to end for lumen 26a in tube 68 and permitting the materials to be suctioned therethrough.

The other tube 70 is connected for only a portion of its length to tube 68. The end to be inserted into the patient terminates in an opening 72 which is spaced from the openings 48a and 32a in lumen 68. An appropriate side opening 50a is provided adjacent to opening 72 in tube 70. The other end of tube 70 is open to receive an end 58a of a conventional connector 60a for a source of air or oxygen. The connector 60a has a passageway therethrough thus providing a pathway for oxygen or air through lumen 28a and tube 70 and into the patient through openings 72 and 50a. The number of openings in the end of tubes 68 and 70 which are inserted into the tracheal passageway of the patient is once again a matter of choice as with the previously discussed embodiment. Also, tube 70 is provided with a free end portion 56a which corresponds to connector 56 of the previously discussed embodiment in providing for ease of connection for the end portion of tube 24a as well as tube 24 to separate sources of suction and oxygen. Also, it makes possible the separation of the two end portions to avoid interference between the suctioning action and the air supply action.

In FIG. 7, an alternative form of connector 74 is depicted. The connector 74 is a one piece integrally formed member that can be constructed of an inexpensive material such as molded plastic. It includes a body portion 76 with one through passageway 78 for communication on one end with one lumen 80 in tube 82 and on the other end to a conventional source of suction. Appropriate ribs 84 are on the surface of body 76 to facilitate the connection to the source of suction. A second through passageway 86 is in body 76 and extends separately through the body and at an angle to the first passageway 78. It communicates at one end with the other lumen 88 in tube 82 and on the other end with a conventional source of oxygen. Once again, a rib 90 is on the outer surface of body 76 in position to facilitate connection to the source of oxygen. Tube 82 can be the same or similar to tubes 24 and 24a of the previously discussed embodiments and can be connected to connector 74 in any conventional manner such as insertion and frictional interengagement.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

We claim:

1. A catheter for use in simultaneously oxygenating and aspirating a patient comprising; an elongated flexible tube arrangement adapted to have at least one end portion extended into the tracheal/bronchial passage of a patient, the tube arrangement having two separate lumens therethrough, one lumen having an opening through one end portion and a plurality of holes through the side of said one end portion and adapted to be connected at the other end of the tube to a source of suction to permit aspiration of material from the patient through the one lumen, and the other lumen being closed at the one end and having a plurality of holes through the side of its end portion and adapted to be connected at the other end to a source of oxygen to permit the oxygenating of the patient through the other lumen while the patient is aspirated through the one lumen enabling the separated lumens to operate independent of one another, said side holes in the one lumen being separated from said side holes in the other lumen to facilitate independent simultaneous oxygenating and suctioning of the patient, and the tube arrangement having a smooth outer surface along a continuous arc at least along the one end portion adapted to extend into the tracheal/bronchial passage of the patient thus alleviating patient trauma.

2. The invention in accordance with claim 1 wherein the tube arrangement is one integrally formed tube with separate side by side lumens extending through the tube.

3. The invention in accordance with claim 2 wherein the other lumen terminates adjacent the other end in an aperture in the side wall of the tube arrangement, a connector tube having a passageway therethrough extended through the side opening in fixed position and in fluid communication with the other lumen, the other end of the connector tube having an opening therein for attachment to a conventional connector for a source of oxygen or air.

4. The invention in accordance with claim 2 wherein the other end of the tube arrangement having an opening in the end edge thereof in communication with the one lumen, the opening in the edge being dimensioned to receive one end of a conventional connector for a source of suction for aspiration purposes.

5. The invention in accordance with claim 1 wherein the tube arrangement is formed of two separate tubes interconnected for at least a substantial portion of their lengths and formed with the one lumen extending through one of the tubes and the other lumen extending to the other of the tubes in side by side relationship.

6. The invention in accordance with claim 1 wherein an integral one piece connector is attached to the other end of both lumens, the connector having a first passageway therethrough for communication with the one lumen on one end and with a source of suction on the other end and a second separate passageway therethrough for connection with the other lumen in one end and with a source of oxygen on the other end, the connector having means thereon for separate connection to a source of suction and a source of oxygen to provide communication between the source of suction and the source of oxygen and the lumens through the separate passageways.

* * * * *